(12) United States Patent
Mujwid et al.

(10) Patent No.: US 12,357,463 B2
(45) Date of Patent: *Jul. 15, 2025

(54) PUMP BULB WITH CONTROL FEATURES

(71) Applicant: Boston Scientific Scimed, Inc., Maple Grove, MN (US)

(72) Inventors: James Ryan Mujwid, Hudson, WI (US); Ryan Earl Fredrick, Eden Prairie, MN (US); Mark Edward DiLoreto, Chaska, MN (US); John Anders Bostrom, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/309,938

(22) Filed: May 1, 2023

(65) Prior Publication Data

US 2023/0263634 A1  Aug. 24, 2023

Related U.S. Application Data

(63) Continuation of application No. 17/645,176, filed on Dec. 20, 2021, now Pat. No. 11,672,663, which is a continuation of application No. 16/866,960, filed on May 5, 2020, now Pat. No. 11,234,824.

(60) Provisional application No. 62/845,012, filed on May 8, 2019.

(51) Int. Cl.
*A61F 2/26* (2006.01)

(52) U.S. Cl.
CPC ........ *A61F 2/26* (2013.01); *A61F 2230/0071* (2013.01)

(58) Field of Classification Search
CPC .......................... A61F 2/26; A61F 2230/0071
See application file for complete search history.

(56) References Cited

U.S. PATENT DOCUMENTS

| 4,566,446 A | * | 1/1986 | Fogarty ............... A61F 2/26 600/40 |
|---|---|---|---|
| 4,881,530 A | | 11/1989 | Trick et al. |
| D323,713 S | | 2/1992 | Arioka et al. |
| 5,167,611 A | | 12/1992 | Cowan |

(Continued)

FOREIGN PATENT DOCUMENTS

| WO | 2020112443 A1 | 6/2020 |
|---|---|---|
| WO | 2022175722 A1 | 8/2022 |
| WO | 2023282883 A1 | 1/2023 |

OTHER PUBLICATIONS

International Search Report and Written Opinion for Application No. PCT/US2019/060938, mailed on Apr. 14, 2020, 11 pages.

(Continued)

*Primary Examiner* — Samuel G Gilbert
(74) *Attorney, Agent, or Firm* — Brake Hughes Bellermann LLP

(57) ABSTRACT

According to an aspect, an inflatable implant includes a fluid reservoir configured to hold fluid; an inflatable member; and a pump assembly configured to transfer fluid from the fluid reservoir to the inflatable member, the pump assembly including a pump bulb, the pump bulb having an outer surface, the pump bulb having a horizontal projection disposed on the outer surface and a vertical projection disposed on the outer surface.

20 Claims, 10 Drawing Sheets

(56) References Cited

U.S. PATENT DOCUMENTS

| | | |
|---|---|---|
| D490,896 S | 6/2004 | Bogazzi |
| D602,881 S | 10/2009 | Lando et al. |
| 7,914,439 B2 | 3/2011 | Kuyava et al. |
| D652,137 S | 1/2012 | Nino et al. |
| 8,276,591 B2 | 10/2012 | Henkel et al. |
| D678,217 S | 3/2013 | Helm |
| 8,491,462 B2 | 7/2013 | Chechik |
| 8,617,050 B2 | 12/2013 | Morningstar |
| 8,684,910 B2 | 4/2014 | Chechik |
| 8,740,769 B2 | 6/2014 | Chechik |
| 8,801,594 B2 | 8/2014 | Fogarty |
| 8,818,512 B2 | 8/2014 | Peddicord |
| 8,939,889 B1 * | 1/2015 | Chechik ............ A61F 2/26 600/40 |
| D725,271 S | 3/2015 | Chechik |
| D725,777 S | 3/2015 | Chechik |
| D739,530 S | 9/2015 | Chechik |
| 9,211,173 B2 | 12/2015 | Morningstar |
| 9,907,653 B2 | 3/2018 | Taylor |
| D818,972 S | 5/2018 | Tang et al. |
| 10,660,757 B2 | 5/2020 | Taylor |
| D888,941 S | 6/2020 | Scrimgeour et al. |
| D917,404 S | 4/2021 | Xu |
| 10,980,637 B2 | 4/2021 | Felton et al. |
| D921,889 S | 6/2021 | Milella et al. |
| D921,890 S | 6/2021 | Milella et al. |
| D943,538 S | 2/2022 | Shi |
| 11,234,824 B2 * | 2/2022 | Mujwid ............ A61F 2/26 |
| 11,337,814 B2 | 5/2022 | Mujwid et al. |
| D979,555 S | 2/2023 | Chen et al. |
| 11,672,663 B2 * | 6/2023 | Mujwid ............ A61F 2/26 600/40 |
| D1,010,120 S | 1/2024 | Harvey et al. |
| 2002/0082709 A1 | 6/2002 | Almli et al. |
| 2004/0138523 A1 * | 7/2004 | Kuyava ............ A61F 2/26 600/40 |
| 2006/0135845 A1 * | 6/2006 | Kuyava ............ A61F 2/26 600/40 |
| 2007/0142700 A1 | 6/2007 | Fogarty et al. |
| 2015/0151042 A1 | 6/2015 | Han |
| 2018/0318085 A1 | 11/2018 | Felton et al. |
| 2022/0117739 A1 | 4/2022 | Mujwid et al. |

OTHER PUBLICATIONS

International Search Report and Written Opinion for PCT Application No. PCT/US2020/031656, mailed on Jul. 30, 2020, 16 pages.

* cited by examiner

PUMP BULB WITH CONTROL FEATURES

CROSS-REFERENCE TO RELATED APPLICATIONS

This application is a continuation of, and claims priority to, U.S. patent application Ser. No. 17/645,176, filed on Dec. 20, 2021, entitled "PUMP BULB WITH CONTROL FEATURES", which claims priority to U.S. patent application Ser. No. 16/866,960, filed on May 5, 2020, entitled "PUMP BULB WITH CONTROL FEATURES", now U.S. Pat. No. 11,234,824, which claims priority to U.S. Patent Application No. 62/845,012, filed on May 8, 2019, entitled "PUMP BULB WITH CONTROL FEATURES", the disclosures of which are incorporated by reference herein in their entirety.

TECHNICAL FIELD

This disclosure relates generally to bodily implants and more specifically to bodily implants, such as penile prosthesis that includes a pump bulb assembly.

BACKGROUND

One treatment for male erectile dysfunction is the implantation of a penile prosthesis that mechanically erects the penis. Some existing penile prostheses include inflatable cylinders or members that can be inflated or deflated using a pump mechanism. The pump mechanism pulls fluid from a fluid reservoir and then transfers the fluid to the inflatable members. The pump mechanism may include a valve body that is used by patients as a place to hold the device while they are pumping the device to achieve inflation. The pump mechanism may also include a pump bulb assembly. However, according to some existing designs, some patients may have difficulty orienting the pump bulb assembly, actuating the pump bulb, or locating the deflation mechanism.

SUMMARY

According to an aspect, an inflatable implant includes a fluid reservoir configured to hold fluid; an inflatable member; and a pump assembly configured to transfer fluid from the fluid reservoir to the inflatable member, the pump assembly including a pump bulb, the pump bulb having an outer surface, the pump bulb having a horizontal projection disposed on the outer surface and a vertical projection disposed on the outer surface.

In some embodiments, the pump bulb includes a plurality of horizontal projections disposed on the outer surface. In some embodiments, the pump bulb includes at least 4 horizontal projections disposed on the outer surface. In some embodiments, the pump bulb includes at least 6 horizontal projections disposed on the outer surface. In some embodiments, the pump bulb includes a plurality of vertical projections disposed on the outer surface. In some embodiments, the pump bulb includes at least 4 vertical projections disposed on the outer surface. In some embodiments, the pump bulb includes at least 6 vertical projections disposed on the outer surface.

In some embodiments, the horizontal projection has a height, a width, and a length, the length of the horizontal projection being greater than the width of the horizontal projection, the length of the horizontal projection defining an axis, the vertical projection has a height, a width, and a length, the length of the vertical projection being greater than the width of the vertical projection, the length of the vertical projection defining an axis, the axis of the horizontal projection being substantially perpendicular to the axis of the vertical projection.

In some embodiments, the horizontal projection includes a curved portion.

In some embodiments, the pump bulb has a first end portion, a second end portion, and a middle portion disposed between the first end portion and the second end portion, the first end portion has a first size, the middle portion has a second size, the first size being greater than the second size. In some embodiments, the pump bulb has a first end portion, a second end portion, and a middle portion disposed between the first end portion and the second end portion, the first end portion has a first size, the middle portion has a second size, the second end portion has a third size, the first size being greater than the second size, the third size being greater than the second size.

In some embodiments, the pump bulb is configured to be disposed within a scrotum of a patient. In some embodiments, the implant is a penile implant. In some embodiments, the implant includes a first inflatable cylinder and a second inflatable cylinder. In some embodiments, the implant includes an actuator configured to place the implant in an inflate mode or a deflate mode.

In another aspect, an inflatable implant includes a fluid reservoir configured to hold fluid; an inflatable member; and a pump assembly configured to transfer fluid from the fluid reservoir to the inflatable member, the pump assembly including a pump bulb, the pump bulb having an outer surface, the pump bulb having a first horizontal projection disposed on the outer surface and a second horizontal projection disposed on the outer surface.

In some embodiments, the pump bulb has a first end portion and a second end portion opposite the first end portion, the first horizontal projection being disposed proximal the first end portion, the second horizontal projection being disposed proximal the second end portion. In some embodiments, the first horizontal projection is offset horizontally and vertically from the second horizontal projection.

In some embodiments, the pump bulb has a middle portion disposed between the first end portion and the second end portion, the first end portion has a first size, the middle portion has a second size, the first size being greater than the second size. In some embodiments, the pump bulb has a middle portion disposed between the first end portion and the second end portion, the first end portion has a first size, the middle portion has a second size, the second end portion has a third size, the first size being greater than the second size, the third size being greater than the second size.

In some embodiments, the pump bulb is configured to be disposed within a scrotum of a patient. In some embodiments, the first horizontal projection is disposed in a first row of horizontal projections, the second horizontal projection is disposed in a second row of horizontal projections, the pump bulb including a third row of horizontal projections.

According to another aspect, an inflatable implant includes a fluid reservoir configured to hold fluid; an inflatable member; and a pump assembly configured to transfer fluid from the fluid reservoir to the inflatable member, the pump assembly including a pump bulb, the pump bulb having an outer surface, the pump bulb having a first horizontal projection disposed on the outer surface, the first horizontal projection forms a ring around the outer surface.

In some embodiments, the pump bulb includes a second horizontal projection disposed on the outer surface, the second horizontal projection forms a ring around the outer surface.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are directed to bodily implants. For example, in some embodiments, the bodily implant is configured to be disposed within a pelvic region of a patient. For example, the bodily implant may be a penile implant. In other embodiments, the implant is configured to be disposed within a different portion of the body of the patient. The term patient or user may hereafter be used for a person who benefits from the medical device or the methods disclosed in the present disclosure. For example, the patient can be a person whose body is implanted with the medical device.

Figure 1:
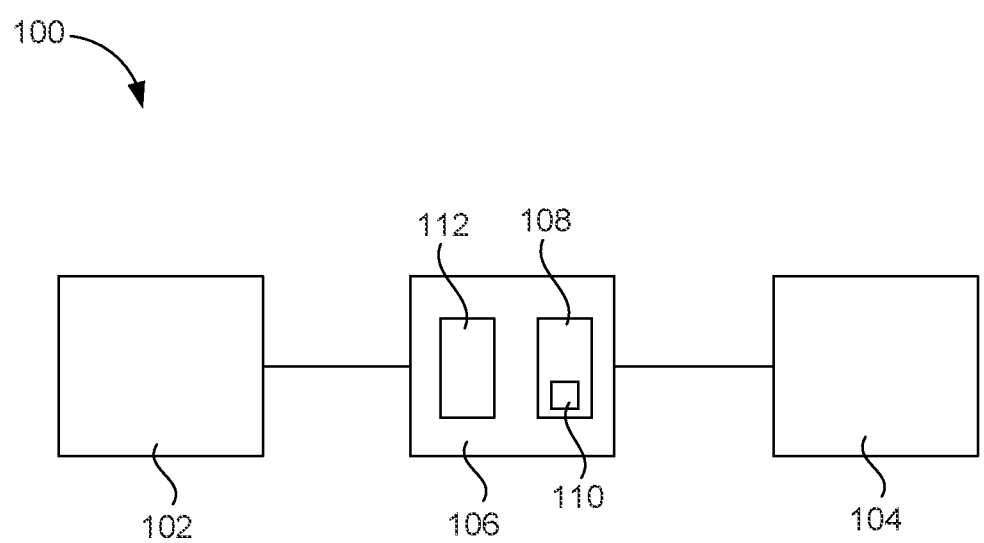
FIG. 1 schematically illustrates an inflatable implant according to an embodiment.

FIG. 1 schematically illustrates a bodily implant 100. In the illustrated embodiment, the implant is an inflatable bodily implant. The bodily implant includes a fluid reservoir 102, an inflatable member 104, and a pump assembly 106. The fluid reservoir 102 is operatively coupled to the pump assembly 106 and the pump assembly 106 is operatively coupled to the inflatable member 104. The pump assembly 106 is configured to transfer fluid between the fluid reservoir 102 and the inflatable member 104 according to an aspect.

In some embodiments, the implant 100 is a penile implant. In some such embodiments, the inflatable member 104 may be implanted into the corpus cavernosae of the user, the fluid reservoir 102 may be implanted in the abdomen or pelvic cavity of the user (e.g., the fluid reservoir 102 may be implanted in the lower portion of the user's abdominal cavity or the upper portion of the user's pelvic cavity), and the pump assembly 106 may be implanted in the scrotum of the user.

The pump assembly 106 includes a pump bulb 108 and an actuator or a deflation mode actuator 112. In an inflation mode, the user may operate the pump bulb 108 (e.g., squeeze the pump bulb 108, release, then squeeze again, etc.) to transfer fluid from the fluid reservoir 102 to the pump assembly 106, and from the pump assembly 106 to the inflatable member 104 such that a desired rigidity is achieved in the inflatable member 104. In order to deflate the inflatable member 104, the user may locate the deflation mode actuator 112, and activate the deflation mode actuator 112 to place the implant 100 in a deflation mode.

In some embodiments, the deflation mode actuator 112 is movably coupled to a pump assembly or a valve body. In some examples, the deflation mode actuator 112 includes a protrusion, that when pressed, causes the valve body to define a fluid passageway from the inflatable member 104 to the fluid reservoir 102 in order to deflate the inflatable member 104. In some examples, the deflation mode actuator 112 includes a push rod or button. In some examples, the user presses the deflation mode actuator 112 once (e.g., does not need to hold the deflation mode actuator 112) to cause fluid to drain from the inflatable member 104.

The pump bulb 108 may be a flexible member defining a cavity. In some embodiments, the pump bulb 108 is coupled to and extends from the valve body. The pump bulb 108 may be a squeeze pump. The pump bulb 108 may use suction and pressure to move the fluid in and out of the cavity of the pump bulb 108 in the inflation mode. For example, the user may depress or squeeze the pump bulb 108 to expel the fluid out of the cavity, and, when the flexible member returns to its original shape, the resulting suction pushes the fluid into the cavity of the pump bulb 108. In some examples, the pump bulb 108 may have a bulb spring rate that is designed to refill the pump bulb 108 in a selected time frame.

In the illustrated embodiment, the pump bulb 108 includes a control feature 110. The control feature 110 is configured to allow the user to locate and grasp the pump bulb 108 during use of the device. For example, when the implant 100 is disposed within the body of the patient, the patient can locate the pump bulb 108 by feeling for the control feature 110. In some embodiments, the control feature 110 is shaped or otherwise configured to allow the user to understand the orientation of the implant within the body. Additionally, in some embodiments, the control feature 110 may facilitate the actuation of the pump bulb. For example, in some embodiments, the control feature 110 may allow or facilitate the user to actuate the pump bulb 108 by grasping the pump bulb 110 with a full hand or with a few fingers or either method.

In some embodiments, the control feature 110 is disposed on an outer surface of the pump bulb. For example, in some embodiments, the pump bulb 108 includes an inner surface that defines an internal channel or cavity. The outer surface is disposed opposite the inner surface. The control feature 110 may extend from, protrude, or otherwise be disposed on the outer surface of the pump bulb 108.

In some embodiments, the control feature 110 is a tactile feature. In some embodiments, the control feature 110 is a single projection or member. In other embodiments, the control feature 110 is a series of projections. In some embodiments, the control feature 110 is a series of projections that are arranged in a specific pattern.

In some embodiments, the pump bulb 108 is formed of an implantable grade silicone. In some embodiments, the control feature 110 is integrally or unitarily formed with the pump bulb 108. In other embodiments, the control feature 110 is formed separately from the pump bulb 108 and is coupled to the pump bulb 108. For example, in some embodiments, the control feature 110 may be coupled to the outer surface of the pump bulb 108 using an adhesive.

In some embodiments, the control feature 110 extends from the outer surface of the pump bulb 108 a sufficient distance such that bodily tissue does not surround the pump bulb to hide or mask the control feature 110. In other words, in some embodiments, the control feature 110 extends such that tissue encapsulation of the implant 100 or the pump bulb 108 does not prevent the user from feeling or detecting the control feature 110.

Figure 2:
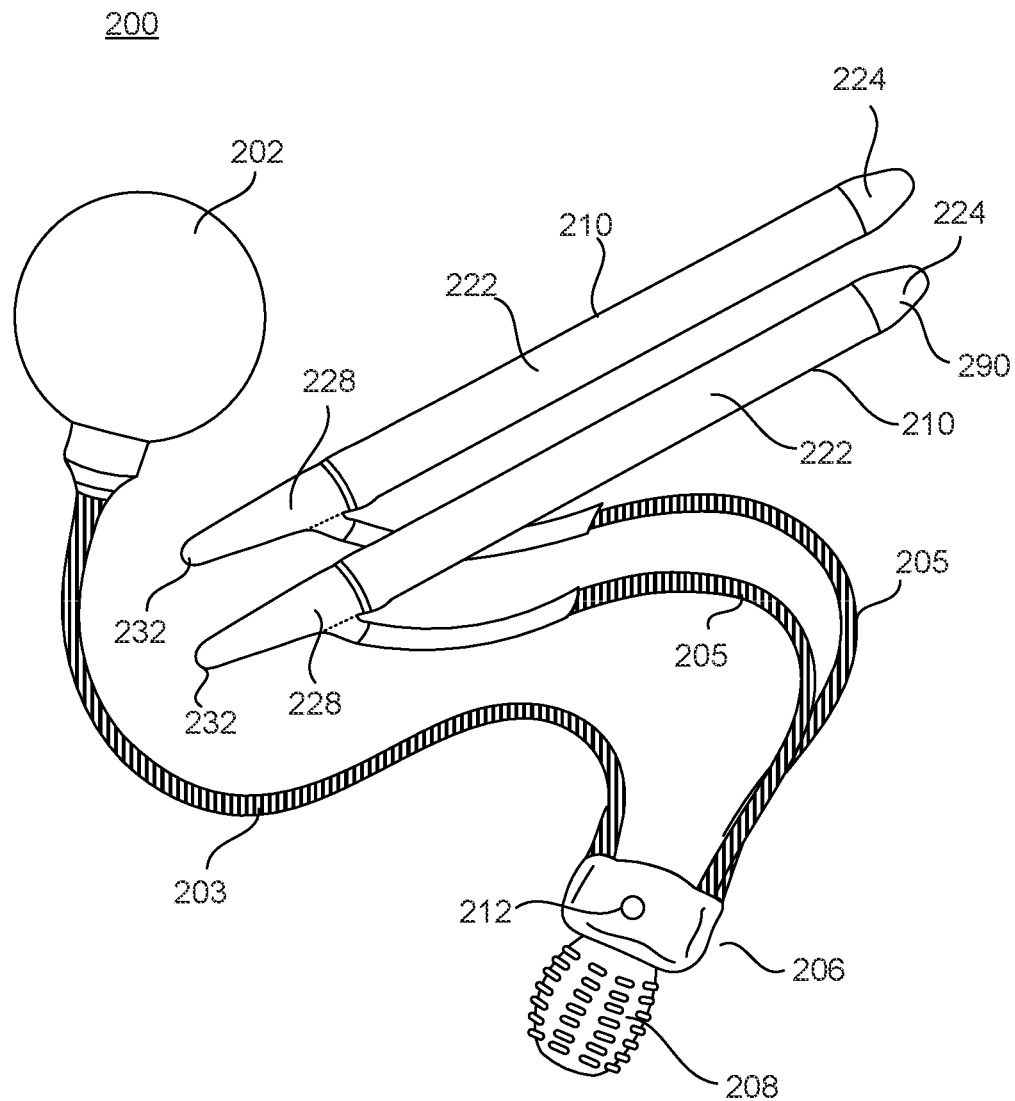
FIG. 2 illustrates an inflatable penile implant according to an embodiment.

FIG. 2 illustrates an inflatable penile prosthesis or implant 200 having a pump assembly 206 according to an aspect. The penile prosthesis 200 may include a pair of inflatable cylinders 210, and the inflatable cylinders 210 are configured to be implanted in a penis of the patient. For example, one of the inflatable cylinders 210 may be disposed on one side of the penis, and the other inflatable cylinder 210 may be disposed on the other side of the penis. Each inflatable cylinder 210 may include a first end portion 224, a cavity or inflation chamber 222, and a second end portion 228 having a rear tip 232.

The pump assembly 206 may be implanted into the patient's scrotum. A pair of conduit connectors 205 may attach the pump assembly 206 to the inflatable cylinders 210 such that the pump assembly 206 is in fluid communication with the inflatable cylinders 210. Also, the pump assembly 206 may be in fluid communication with a fluid reservoir 202 via a conduit connector 203. The fluid reservoir 202 may be implanted into the user's abdomen. The inflation chamber or portion 222 of the inflatable cylinder 210 may be disposed within the penis. The first end portion 224 of the inflatable cylinder 210 may be at least partially disposed within the crown portion of the penis. The second end portion 228 may be implanted into the patient's pubic region with the rear tip 232 proximate the pubic bone.

In order to implant the inflatable cylinders 210, the surgeon may first prepare the patient. The surgeon often makes an incision in the penoscrotal region, e.g., where the base of the penis meets with the top of the scrotum. From the penoscrotal incision, the surgeon may dilate the patient's corpus cavernosae to prepare the patient to receive the inflatable cylinders 210. The corpus cavernosum is one of two parallel columns of erectile tissue forming the dorsal part of the body of the penis, e.g., two slender columns that extend substantially the length of the penis. The surgeon will also dilate two regions of the pubic area to prepare the patient to receive the second end portion 228. The surgeon may measure the length of the corpora cavernosae from the incision and the dilated region of the pubic area to determine an appropriate size of the inflatable cylinders 210 to implant.

After the patient is prepared, the penile prosthesis 200 is implanted into the patient. The tip of the first end portion 224 of each inflatable cylinder 210 may be attached to a suture. The other end of the suture may be attached to a needle member (e.g., Keith needle). The needle member is inserted into the incision and into the dilated corpus cavernosum. The needle member is then forced through the crown of the penis. The surgeon tugs on the suture to pull the inflatable cylinder 210 into the corpus cavernosum. This is done for each inflatable cylinder 210 of the pair. Once the inflation chamber 222 is in place, the surgeon may remove the suture from the tip. The surgeon then inserts the second end portion 228. The surgeon inserts the rear end of the inflatable cylinder 210 into the incision and forces the second end portion 228 toward the pubic bone until each inflatable cylinder 210 is in place.

A pump bulb 208 of the pump assembly 206 may be squeezed or depressed by the user in order to facilitate the transfer of fluid from the fluid reservoir 202 to the inflatable cylinders 210. For example, in the inflation mode, while the user is operating the pump bulb 208, the pump bulb 208 may receive the fluid from the fluid reservoir 202, and then output the fluid to the inflatable cylinders 210. When the user switches to the deflation mode, at least some of the fluid can automatically be transferred back to the fluid reservoir 202 (due to the difference in pressure from the inflatable cylinders 210 to the fluid reservoir 202). Then, the user may squeeze the inflatable cylinders 210 to facilitate the further transfer of fluid through the pump to the fluid reservoir 202.

In the illustrated embodiment, the pump assembly 206 includes an actuation member 212. The actuation member 212 may be used by the patient to toggle or switch the penile implant 200 from its inflate mode to its deflate mode.

Figure 3:
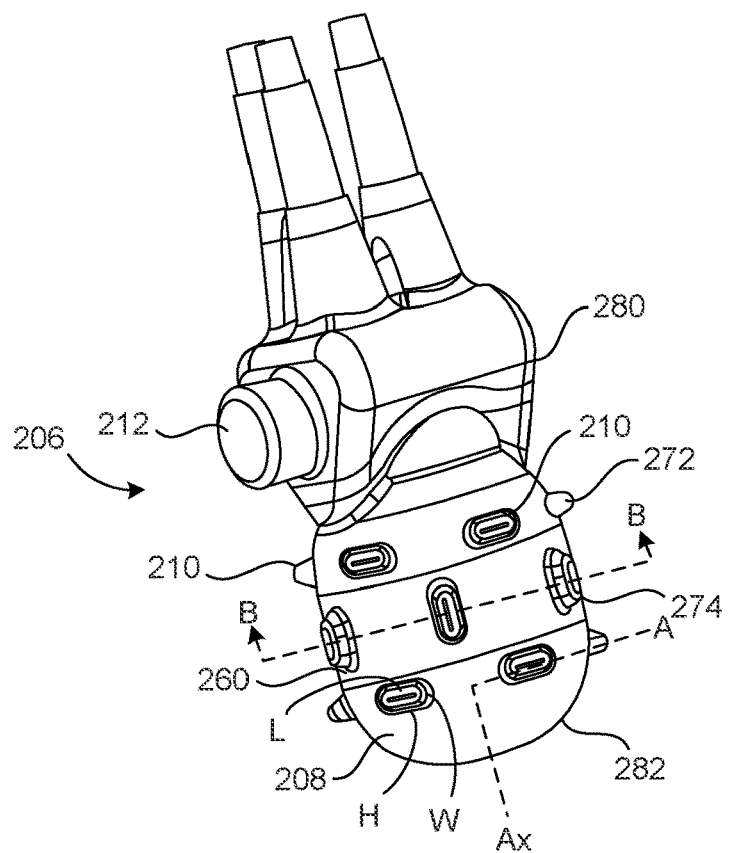
FIG. 3 is a perspective view of the pump bulb assembly of the penile implant of FIG. 2.
Figure 4:
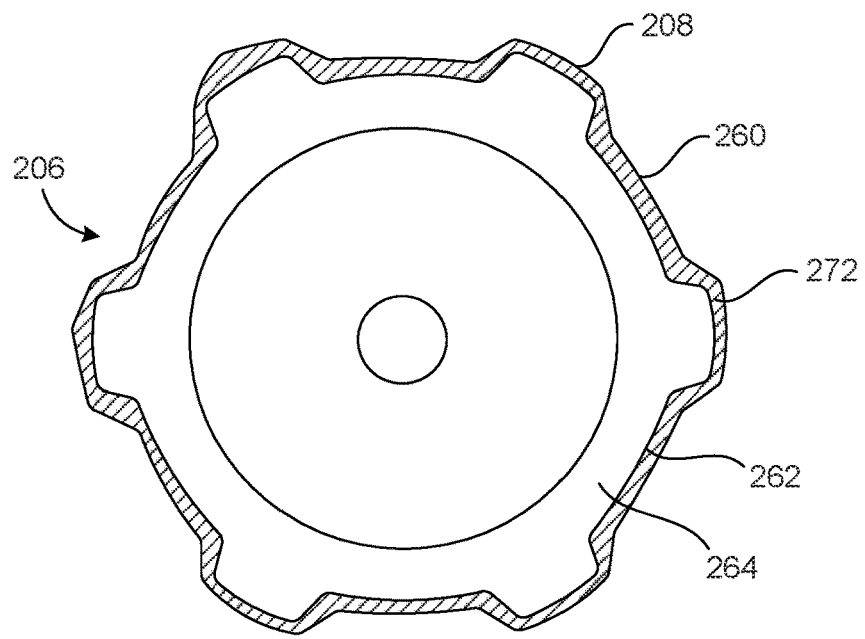
FIG. 4 is a cross-sectional view of the pump bulb assembly of the penile implant of FIG. 2, taken along line B-B of FIG. 3.

FIGS. 3 and 4 illustrate the pump assembly 206. In the illustrated embodiment, the pump bulb 208 includes an outer surface 260. The pump bulb 208 also includes an inner surface 262. The inner surface 262 is disposed opposite the outer surface 260. The inner surface 262 defines the cavity 264 that is configured to house or receive the fluid as it is passed through the penile implant 200.

The pump assembly 206 includes a control feature or member 210. In the illustrated embodiment, the pump assembly 206 includes a plurality of projections that form the control feature or member 210. The pump assembly 206 includes a plurality of horizontal projections 272 and a plurality of vertical projections 274. The horizontal projections 272 and the vertical projections are coupled to and extend from the outer surface 260 of the pump bulb 208. In some embodiments, the horizontal projections 272 and the vertical projections 274 are integrally or unitarily formed with the pump bulb 208.

In the illustrated embodiment, the projections 272 and 274 each have a height H (the distance that the projections 272 and 274 extend from the outer surface 260 of the pump bulb 208), a length L, and a width W. The lengths of the projections 272 and 274 are larger or greater than the widths of the projections 272 and 274. In the illustrated embodiment, the length L of each of the projections defines an axis A of the projections. Specifically, the length L extends along the axis A.

The pump bulb 208 has a first end portion 280 and a second end portion 282 disposed opposite the first end portion 280. The pump bulb 208 defines an axis AX that extends from the first end portion 280 to the second end portion 282. In the illustrated embodiment, the projections 272 and 274 extend substantially linearly in the length direction (along the length L and in the direction of the axis A). The horizontal projections 272 extend (along the length L and in the direction of the axis A) substantially perpendicular to the axis AX of the pump bulb 208 and substantially perpendicular to the axis of the vertical projections 274. The vertical projections 274 extend (along the length) in a direction substantially parallel to the axis AX of the pump bulb 208.

In the illustrated embodiment, the pump assembly includes six horizontal projections 272 and twelve vertical projections 274. In other embodiments, the pump assembly includes a different number of horizontal projections (such as more than twelve or less than twelve). Similarly, in other embodiments, the pump assembly includes a different number of vertical projections (such as more than six or less than six).

In the illustrated embodiment, the horizontal projections 272 and the vertical projections 274 help prevent the pump bulb 208 from slipping from the grip of the user. For example, the horizontal projections 272 may help prevent the pump bulb 208 from slipping vertically and the vertical projections 274 may help prevent the pump bulb from slipping horizontally. The projections may also help prevent the pump bulb 208 from rotating during the pumping or actuation by the user. In some embodiments, the projections 272 and 274 help or facilitate the locating of the deflation mode actuator 212.

Figure 5:
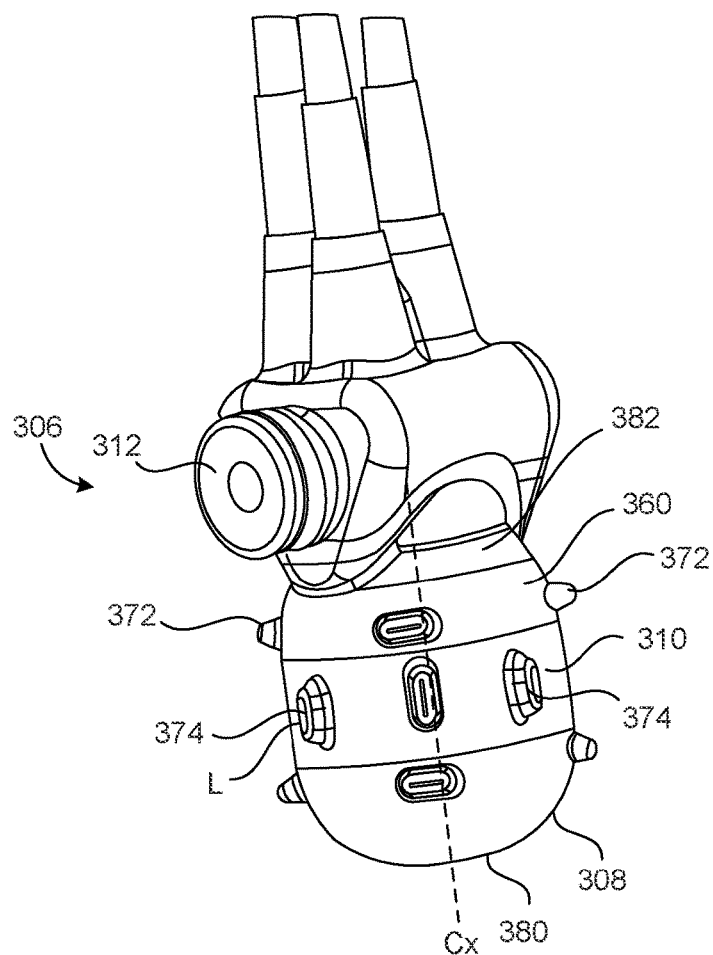
FIGS. 5-12 are perspective views of pump bulb assemblies according to embodiments.

FIG. 5 illustrates a pump assembly 306 of a penile implant according to an embodiment. In the illustrated embodiment, the pump bulb 308 includes an outer surface 360. The pump bulb 308 also includes an inner surface. The inner surface is disposed opposite the outer surface 360. The inner surface defines the cavity that is configured to house or receive the fluid as it is passed through the penile implant.

The pump assembly 306 includes a control feature or member 310. In the illustrated embodiment, the pump assembly 306 includes a plurality of projections that form the control feature or member 310. The pump assembly 306 includes a plurality of horizontal projections 372 and a plurality of vertical projections 374. The horizontal projections 372 and the vertical projections are coupled to and extend from the outer surface 360 of the pump bulb 308. In some embodiments, the horizontal projections 372 and the vertical projections 374 are integrally or unitarily formed with the pump bulb 308.

In the illustrated embodiment, the projections 372 and 374 each have a height H (the distance that the projections 372 and 374 extend from the outer surface 360 of the pump bulb 308), a length L, and a width W. The lengths of the projections 372 and 374 are larger or greater than the widths of the projections 372 and 374. In the illustrated embodiment, the length L of each of the projections defines an axis C of the projections. Specifically, the length L extends along the axis C.

The pump bulb 308 has a first end portion 380 and a second end portion 382 disposed opposite the first end portion 380. The pump bulb 308 defines an axis CX that extends from the first end portion 380 to the second end portion 382. In the illustrated embodiment, the projections 372 and 374 extend substantially linearly in the length direction (along the length L and in the direction of the axis C). The horizontal projections 372 extend (along the length L and in the direction of the axis C) substantially perpendicular to the axis CX of the pump bulb 308 and substantially perpendicular to the axis of the vertical projections 374. The vertical projections 374 extend (along the length) in a direction substantially parallel to the axis CX of the pump bulb 308.

In the illustrated embodiment, the pump assembly includes four horizontal projections 372 and eight vertical projections 374. In other embodiments, the pump assembly includes a different number of horizontal projections (such as more than eight or less than eight). Similarly, in other embodiments, the pump assembly includes a different number of vertical projections (such as more than four or less than four).

In the illustrated embodiment, the horizontal projections 372 and the vertical projections 374 help prevent the pump bulb 308 from slipping from the grip of the user. For example, the horizontal projections 372 may help prevent the pump bulb 308 from slipping vertically and the vertical projections 374 may help prevent the pump bulb from slipping horizontally. The projections may also help prevent the pump bulb 308 from rotating during the pumping or actuation by the user. In some embodiments, the projections 372 and 374 help or facilitate the locating of the deflation mode actuator 312.

Figure 6:
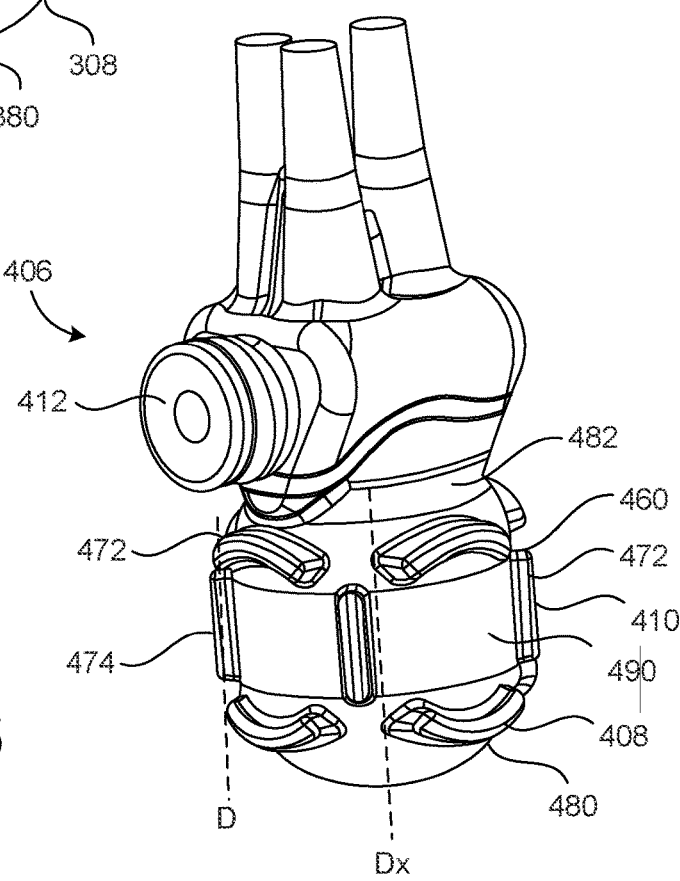

FIG. 6 illustrates a pump assembly 406 of a penile implant according to an embodiment. In the illustrated embodiment, the pump bulb 408 includes an outer surface 460. The pump bulb 408 also includes an inner surface. The inner surface is disposed opposite the outer surface 460. The inner surface defines the cavity that is configured to house or receive the fluid as it is passed through the penile implant.

The pump assembly 406 includes a control feature or member 410. In the illustrated embodiment, the pump assembly 406 includes a plurality of projections that form the control feature or member 410. The pump assembly 406 includes a plurality of horizontal projections 472 and a plurality of vertical projections 474. The horizontal projections 472 and the vertical projections are coupled to and extend from the outer surface 460 of the pump bulb 408. In some embodiments, the horizontal projections 472 and the vertical projections 474 are integrally or unitarily formed with the pump bulb 408.

In the illustrated embodiment, the projections 472 and 474 each have a height H (the distance that the projections 472 and 474 extend from the outer surface 460 of the pump bulb 408), a length L, and a width W. The lengths of the projections 472 and 474 are larger or greater than the widths of the projections 472 and 474. In the illustrated embodiment, the length L of each of the projections defines an axis D of the projections. Specifically, the length L extends along the axis D.

The pump bulb 408 has a first end portion 480 and a second end portion 482 disposed opposite the first end portion 480. The pump bulb 408 defines an axis DX that extends from the first end portion 480 to the second end portion 482. In the illustrated embodiment, the horizontal projections 472 include a curvature in the length direction. In other words, the horizontal projections 472 do not extend linearly in the length direction. The vertical projections 474 extend (along the length) in a direction substantially parallel to the axis DX of the pump bulb 408.

In the illustrated embodiment, the pump assembly includes eight horizontal projections 472 and four vertical projections 474. In other embodiments, the pump assembly includes a different number of horizontal projections (such as more than eight or less than eight). Similarly, in other embodiments, the pump assembly includes a different number of vertical projections (such as more than four or less than four).

As best illustrated in FIG. 6, two of the horizontal projections 472 and two of the vertical projections 474 form a receiving location 490. The receiving location 490 is configured to receive or partially receive a finger or a portion of a hand of a user to facilitate the actuation of the pump bulb 408. The horizontal projections 472 and the vertical projections 474 help prevent the pump bulb 408 from slipping from the grip of the user. For example, the horizontal projections 472 may help prevent the pump bulb 408 from slipping vertically and the vertical projections 474 may help prevent the pump bulb from slipping horizontally. The projections may also help prevent the pump bulb 408 from rotating during the pumping or actuation by the user. In some embodiments, the projections 472 and 474 help or facilitate the locating of the deflation mode actuator 412.

Specifically, as the user grips or feels the projections 472 and 474 on the pump bulb 408, the user understand the orientation of the pump assembly and may then be led or guided to know where the mode actuator 412 is located.

Figure 7:
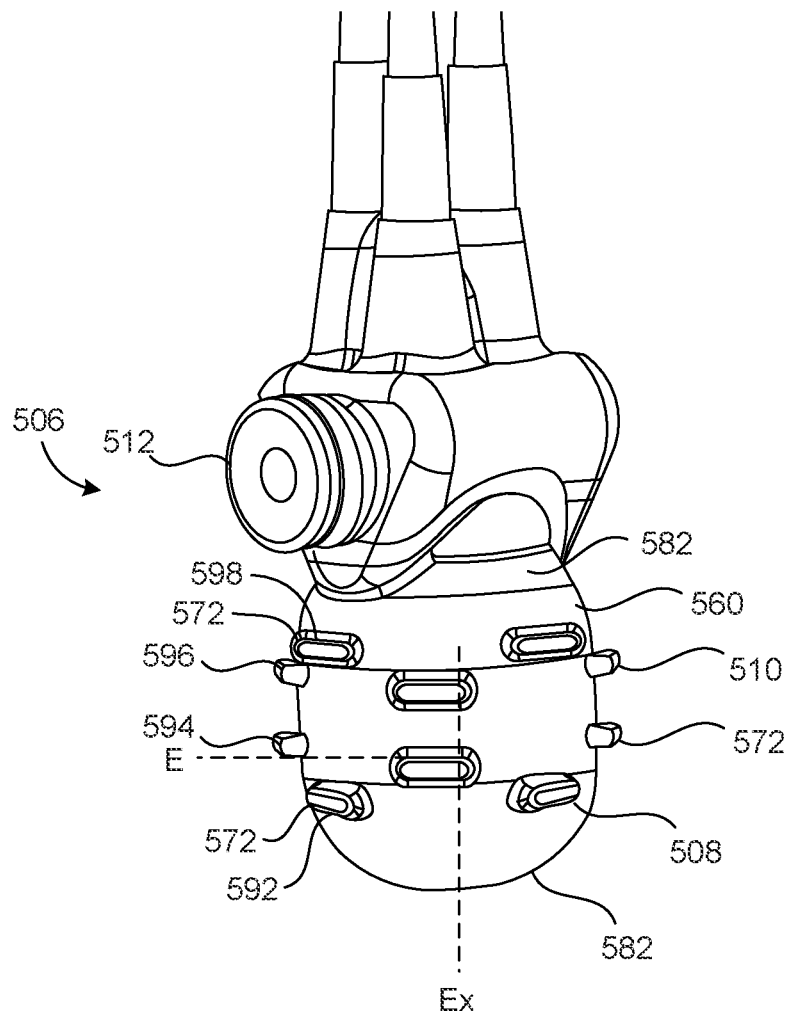

FIG. 7 illustrates a pump assembly 506 of a penile implant according to an embodiment. In the illustrated embodiment, the pump bulb 508 includes an outer surface 560. The pump bulb 508 also includes an inner surface. The inner surface is disposed opposite the outer surface 560. The inner surface defines the cavity that is configured to house or receive the fluid as it is passed through the penile implant.

The pump assembly 506 includes a control feature or member 510. In the illustrated embodiment, the pump assembly 506 includes a plurality of projections that form the control feature or member 510. The pump assembly 506 includes a plurality of horizontal projections 572. The horizontal projections 572 are coupled to and extend from the outer surface 560 of the pump bulb 508. In some embodiments, the horizontal projections 572 are integrally or unitarily formed with the pump bulb 508.

In the illustrated embodiment, the projections 572 each have a height H (the distance that the projections 572 extend from the outer surface 560 of the pump bulb 508), a length L, and a width W. The lengths of the projections 572 are larger or greater than the widths of the projections 572. In the illustrated embodiment, the length L of each of the projections defines an axis E of the projections. Specifically, the length L extends along the axis E.

The pump bulb 508 has a first end portion 580 and a second end portion 582 disposed opposite the first end portion 580. The pump bulb 508 defines an axis EX that extends from the first end portion 580 to the second end portion 582. In the illustrated embodiment, the projections 572 extend substantially linearly in the length direction (along the length L and in the direction of the axis E). In the illustrated embodiment, the axis E is substantially perpendicular to the axis EX.

In the illustrated embodiment, the pump assembly includes a first series of horizontal projections 592, a second series of horizontal projections 594, a third series of horizontal projections 596, and a fourth series of horizontal projections 598. Each series of projections extend around a circumference of the pump bulb 508. In the illustrated embodiment, the first series of projections 592 are disposed proximate or near the first end portion 580 of the pump bulb 508. The fourth series of projections 598 are disposed proximate or near the second end portion 582 of the pump bulb 508. The second series of projections 594 and the third series of projections 596 are disposed between the first series of projections 592 and the fourth series of projections 598. Additionally, in the illustrated embodiment, the second series of projections 594 and third series of projections 596 are aligned with each other. In other words, the projections in the second series of projections 594 are horizontally aligned with projections of the third series of projections 596. The projections of the first series of projections 592 are aligned with the projections of the fourth series of projections 598. The projections of the first series of projections 592 are offset (or not horizontally aligned with) from the projections of the second series of projections 594.

In some embodiments, the pump assembly includes a different number of series of horizontal projections (such as more than four or less than four).

In the illustrated embodiment, the projections 572 may help prevent the pump bulb 508 from slipping during actuation of the pump bulb 508 by the user. The projections may also help prevent the pump bulb 508 from rotating during the pumping or actuation by the user. In some embodiments, the projections 572 help or facilitate the locating of the deflation mode actuator 512.

Figure 8:
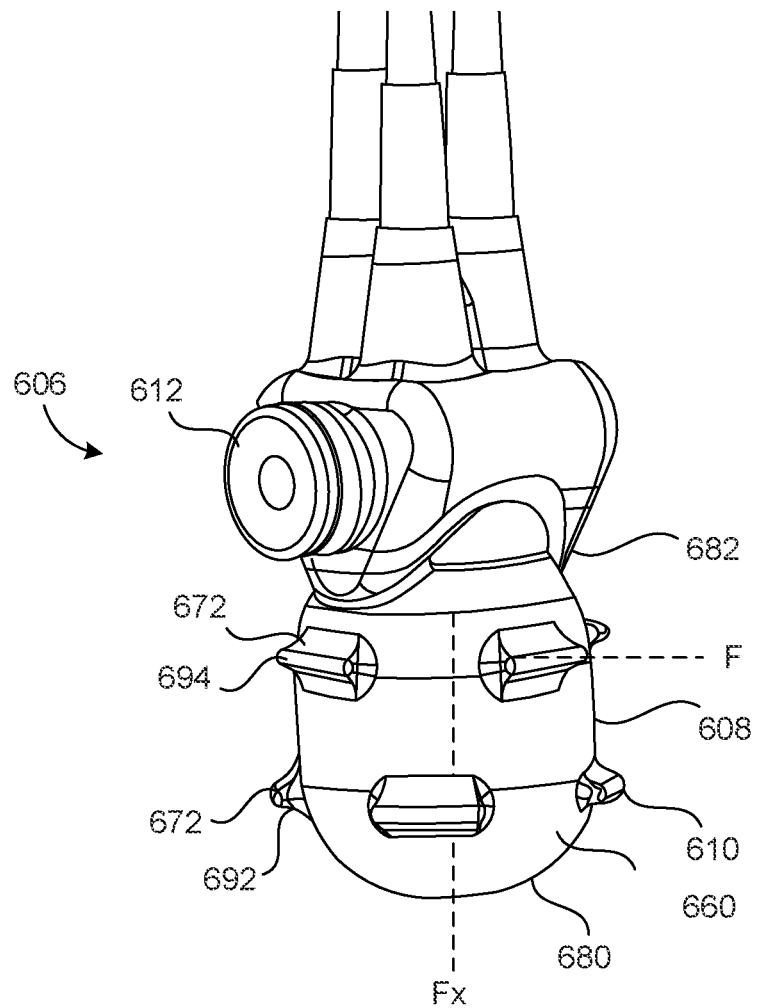

FIG. 8 illustrates a pump assembly 606 of a penile implant according to an embodiment. In the illustrated embodiment, the pump bulb 608 includes an outer surface 660. The pump bulb 608 also includes an inner surface. The inner surface is disposed opposite the outer surface 660. The inner surface defines the cavity that is configured to house or receive the fluid as it is passed through the penile implant.

The pump assembly 606 includes a control feature or member 610. In the illustrated embodiment, the pump assembly 606 includes a plurality of projections that form the control feature or member 610. The pump assembly 606 includes a plurality of horizontal projections 672. The horizontal projections 672 are coupled to and extend from the outer surface 660 of the pump bulb 608. In some embodiments, the horizontal projections 672 are integrally or unitarily formed with the pump bulb 608.

In the illustrated embodiment, the projections 672 each have a height H (the distance that the projections 672 extend from the outer surface 660 of the pump bulb 608), a length L, and a width W. The lengths of the projections 672 are larger or greater than the widths of the projections 672. In the illustrated embodiment, the length L of each of the projections defines an axis F of the projections. Specifically, the length L extends along the axis F.

The pump bulb 608 has a first end portion 680 and a second end portion 682 disposed opposite the first end portion 680. The pump bulb 608 defines an axis FX that extends from the first end portion 680 to the second end portion 682. In the illustrated embodiment, the projections 672 extend substantially linearly in the length direction (along the length L and in the direction of the axis F). In the illustrated embodiment, the axis F is substantially perpendicular to the axis FX.

In the illustrated embodiment, the pump assembly includes a first series of horizontal projections 692 and a second series of horizontal projections 694. Each series of projections extend around a circumference of the pump bulb 608. In the illustrated embodiment, the first series of projections 692 are disposed proximate or near the first end portion 680 of the pump bulb 608. The second series of projections 692 are disposed proximate or near the second end portion 682 of the pump bulb 608. The projections of the first series of projections 692 are offset (or not horizontally aligned with) from the projections of the second series of projections 694.

In some embodiments, the pump assembly includes a different number of series of horizontal projections (such as more than two or less than two).

In the illustrated embodiment, the projections 672 may help prevent the pump bulb 608 from slipping during actuation of the pump bulb 608 by the user. The projections may also help prevent the pump bulb 608 from rotating during the pumping or actuation by the user. In some embodiments, the projections 672 help or facilitate the locating of the deflation mode actuator 612.

Figure 9:
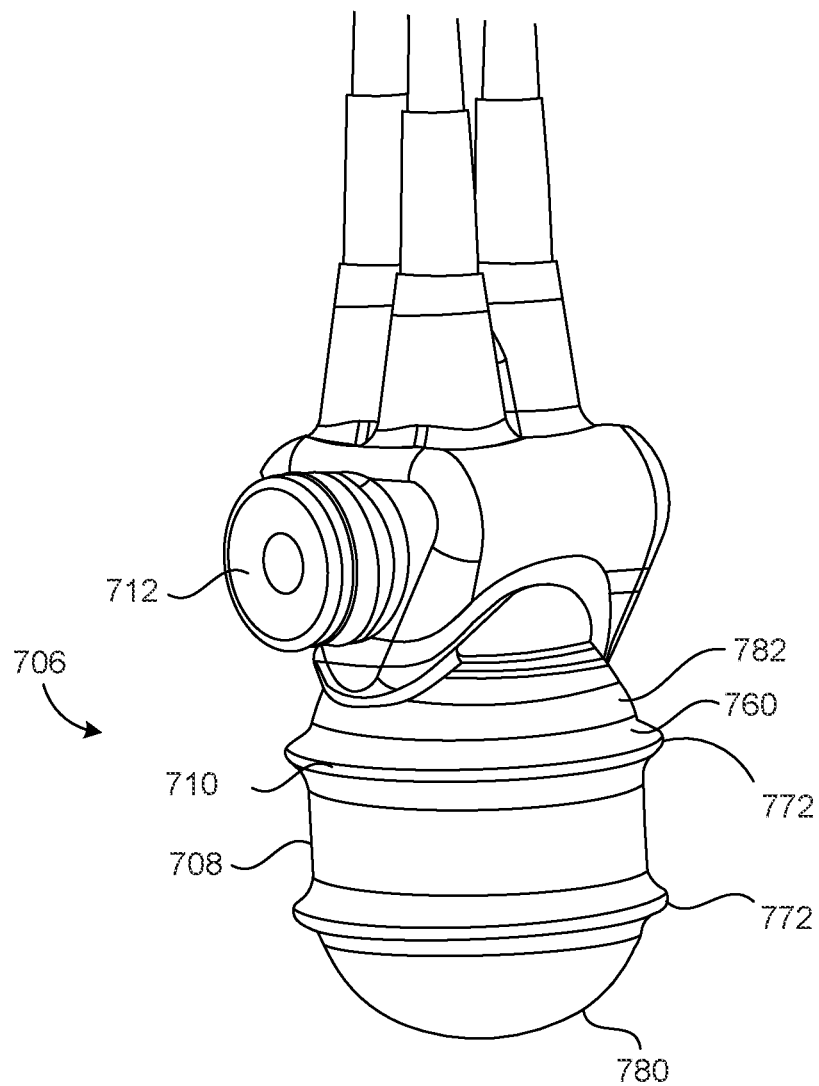

FIG. 9 illustrates a pump assembly 706 of a penile implant according to an embodiment. In the illustrated embodiment, the pump bulb 708 includes an outer surface 760. The pump bulb 708 also includes an inner surface. The inner surface is disposed opposite the outer surface 760. The inner surface defines the cavity that is configured to house or receive the fluid as it is passed through the penile implant.

The pump assembly 706 includes a control feature or member 710. In the illustrated embodiment, the pump assembly 706 includes a plurality of horizontal projections 772 that form the control feature or member 710. The horizontal projections 772 are coupled to and extend from the outer surface 760 of the pump bulb 708. In some embodiments, the horizontal projections 772 are integrally or unitarily formed with the pump bulb 708.

In the illustrated embodiment, the projections 772 form rings that extend around the pump bulb 708. In the illustrated embodiment, the projections 772 form complete rings. In other embodiments, the projections 772 may include breaks or notches or otherwise not form complete rings around the circumference of the pump bulb 708.

The pump bulb 708 has a first end portion 780 and a second end portion 782 disposed opposite the first end portion 780. The pump bulb 708 defines an axis GX that extends from the first end portion 780 to the second end portion 782. In the illustrated embodiment, the projections extend around the pump bulb 708 substantially perpendicularly to the axis GX.

In some embodiments, the pump assembly includes a different number of series of horizontal projections or rings (such as more than two or less than two).

In the illustrated embodiment, the projections 772 may help prevent the pump bulb 708 from slipping during actuation of the pump bulb 708 by the user. The projections may also help prevent the pump bulb 708 from rotating during the pumping or actuation by the user. In some embodiments, the projections 772 help or facilitate the locating of the deflation mode actuator 712.

Figure 10:
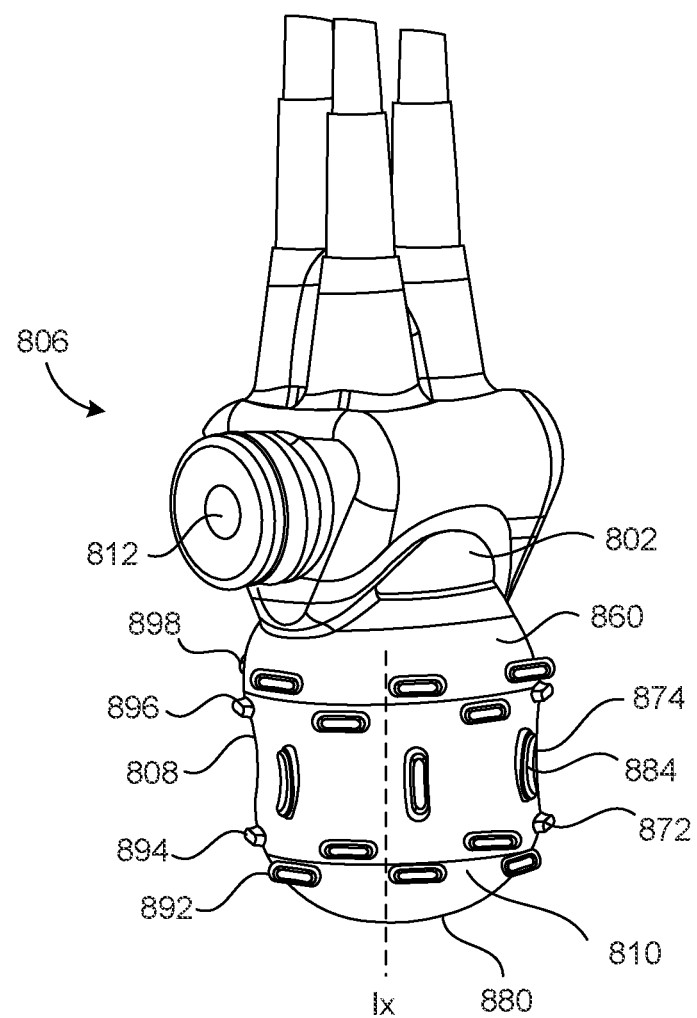

FIG. 10 illustrates a pump assembly 806 of a penile implant according to an embodiment. In the illustrated embodiment, the pump bulb 808 includes an outer surface 860. The pump bulb 808 also includes an inner surface. The inner surface is disposed opposite the outer surface 860. The inner surface defines the cavity that is configured to house or receive the fluid as it is passed through the penile implant.

The pump assembly 806 includes a control feature or member 810. In the illustrated embodiment, the pump assembly 806 includes a plurality of projections that form the control feature or member 810. The pump assembly 806 includes a plurality of horizontal projections 872 and a plurality of vertical projections 874. The horizontal projections 872 are coupled to and extend from the outer surface 860 of the pump bulb 808. In some embodiments, the horizontal projections 872 are integrally or unitarily formed with the pump bulb 808.

In the illustrated embodiment, the projections 872 each have a height H (the distance that the projections 872 extend from the outer surface 860 of the pump bulb 808), a length L, and a width W. The lengths of the projections 872 are larger or greater than the widths of the projections 872. In the illustrated embodiment, the length L of each of the projections defines an axis I of the projections. Specifically, the length L extends along the axis I.

The pump bulb 808 has a first end portion 880 and a second end portion 882 disposed opposite the first end portion 880. The pump bulb 808 defines an axis IX that extends from the first end portion 880 to the second end portion 882. In the illustrated embodiment, the projections 872 extend substantially linearly in the length direction (along the length L and in the direction of the axis I). In the illustrated embodiment, the axis I is substantially perpendicular to the axis IX.

The vertical projections 874 extend substantially perpendicular to the axis I and extend substantially parallel to the axis IX.

In the illustrated embodiment, the pump assembly includes a first series of horizontal projections 892, a second series of horizontal projections 894, a third series of horizontal projections 896, and a fourth series of horizontal projections 898. Each series of projections extends around a circumference of the pump bulb 808. In the illustrated embodiment, the first series of projections 892 are disposed proximate or near the first end portion 880 of the pump bulb 808. The fourth series of projections 898 are disposed proximate or near the second end portion 882 of the pump bulb 808. The second series of projections 894 and the third series of projections 896 are disposed between the first series of projections 892 and the fourth series of projections 898. Additionally, in the illustrated embodiment, the second series of projections 894 and third series of projections 896 are aligned with each other. In other words, the projections in the second series of projections 894 are horizontally aligned with projections of the third series of projections 896. The projections of the first series of projections 892 are aligned with the projections of the fourth series of projections 898. The projections of the first series of projections 892 are offset from (or not horizontally aligned with) the projections of the second series of projections 894.

In some embodiments, the pump assembly includes a different number of series of horizontal projections (such as more than four or less than four).

In the illustrated embodiment, different locations of the pump bulb 808 have different sizes. For example, the diameter of the pump bulb 808 varies at different locations along the pump bulb 808. In the illustrated embodiment, the pump bulb 808 has a first size at the first end portion 880, a second size at the second end portion 882, and a third size at a location 884 that is between the first end portion 880 and the second end portion 882. The first size is larger than the third size. The second size is larger than the third size. In some embodiments, the first size and the second size are the same. In other embodiments, the first size is different than the second size.

In the illustrated embodiment, the projections 872 and 874 and/or the different sizes of the pump bulb 808 may help prevent the pump bulb 808 from slipping during actuation of the pump bulb 808 by the user. The projections and sizes may also help prevent the pump bulb 808 from rotating during the pumping or actuation by the user. In some embodiments, the projections 872 and 874 help or facilitate the locating of the deflation mode actuator 812.

Figure 11:
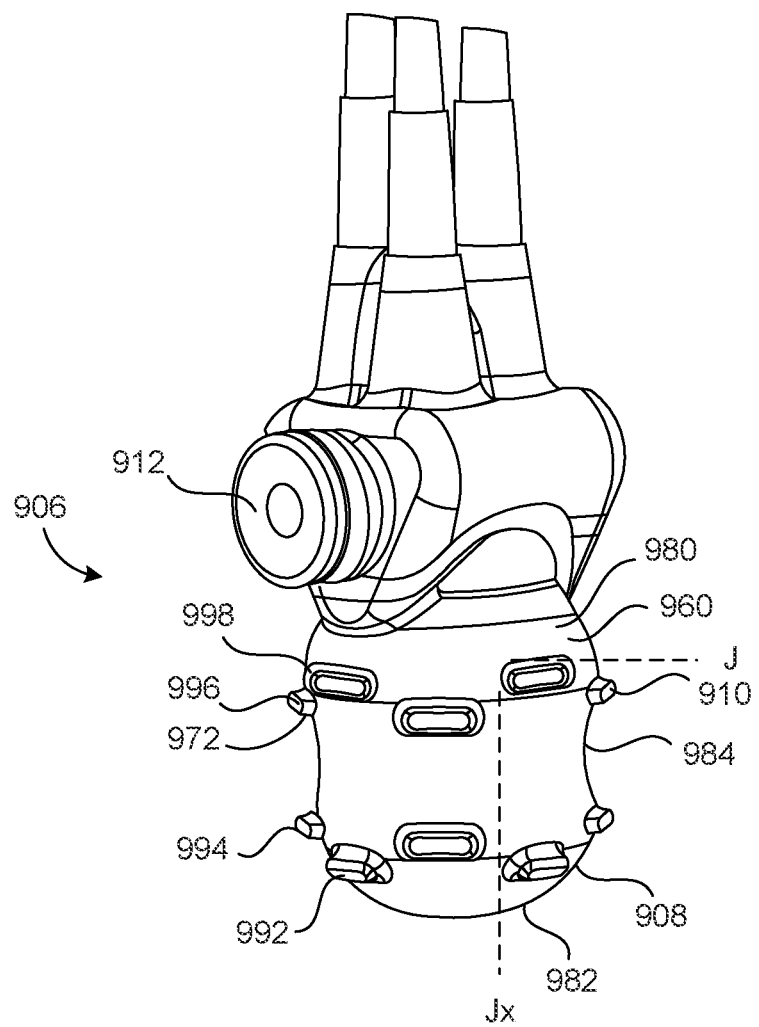

FIG. 11 illustrates a pump assembly 906 of a penile implant according to an embodiment. In the illustrated embodiment, the pump bulb 908 includes an outer surface 960. The pump bulb 908 also includes an inner surface. The inner surface is disposed opposite the outer surface 960. The inner surface defines the cavity that is configured to house or receive the fluid as it is passed through the penile implant.

The pump assembly 906 includes a control feature or member 910. In the illustrated embodiment, the pump assembly 906 includes a plurality of projections that form the control feature or member 910. The pump assembly 906 includes a plurality of horizontal projections 972. The horizontal projections 972 are coupled to and extend from the outer surface 960 of the pump bulb 908. In some embodiments, the horizontal projections 972 are integrally or unitarily formed with the pump bulb 908.

In the illustrated embodiment, the projections 972 each have a height H (the distance that the projections 972 extend from the outer surface 960 of the pump bulb 908), a length L, and a width W. The lengths of the projections 972 are larger or greater than the widths of the projections 972. In the illustrated embodiment, the length L of each of the projections defines an axis J of the projections. Specifically, the length L extends along the axis J.

The pump bulb 908 has a first end portion 980 and a second end portion 982 disposed opposite the first end portion 980. The pump bulb 908 defines an axis JX that extends from the first end portion 980 to the second end portion 982. In the illustrated embodiment, the projections 972 extend substantially linearly in the length direction (along the length L and in the direction of the axis J). In the illustrated embodiment, the axis J is substantially perpendicular to the axis JX.

In the illustrated embodiment, the pump assembly includes a first series of horizontal projections 992, a second series of horizontal projections 994, a third series of horizontal projections 996, and a fourth series of horizontal projections 998. Each series of projections extend around a circumference of the pump bulb 908. In the illustrated embodiment, the first series of projections 992 are disposed proximate or near the first end portion 980 of the pump bulb 908. The fourth series of projections 998 are disposed proximate or near the second end portion 982 of the pump bulb 908. The second series of projections 994 and the third series of projections 996 are disposed between the first series of projections 992 and the fourth series of projections 998. Additionally, in the illustrated embodiment, the second series of projections 994 and third series of projections 996 are aligned with each other. In other words, the projections in the second series of projections 994 are horizontally aligned with projections of the third series of projections 996. The projections of the first series of projections 992 are aligned with the projections of the fourth series of projections 998. The projections of the first series of projections 992 are offset (or not horizontally aligned with) from the projections of the second series of projections 994.

In some embodiments, the pump assembly includes a different number of series of horizontal projections (such as more than four or less than four).

In the illustrated embodiment, different locations of the pump bulb 908 have different sizes. For example, the diameter of the pump bulb 908 varies at different locations along the pump bulb 908. In the illustrated embodiment, the pump bulb 908 has a first size at the first end portion 980, a second size at the second end portion 982, and a third size at a location 984 that is between the first end portion 980 and the second end portion 982. The first size is larger than the third size. The second size is larger than the third size. In some embodiments, the first size and the second size are the same. In other embodiments, the first size is different than the second size.

In the illustrated embodiment, the projections 972 and/or the sizing of the pump bulb 908 may help prevent the pump bulb 908 from slipping during actuation of the pump bulb 908 by the user. The projections and/or the sizing of the pump bulb may also help prevent the pump bulb 908 from rotating during the pumping or actuation by the user. In some embodiments, the projections 972 help or facilitate the locating of the deflation mode actuator 912.

Figure 12:
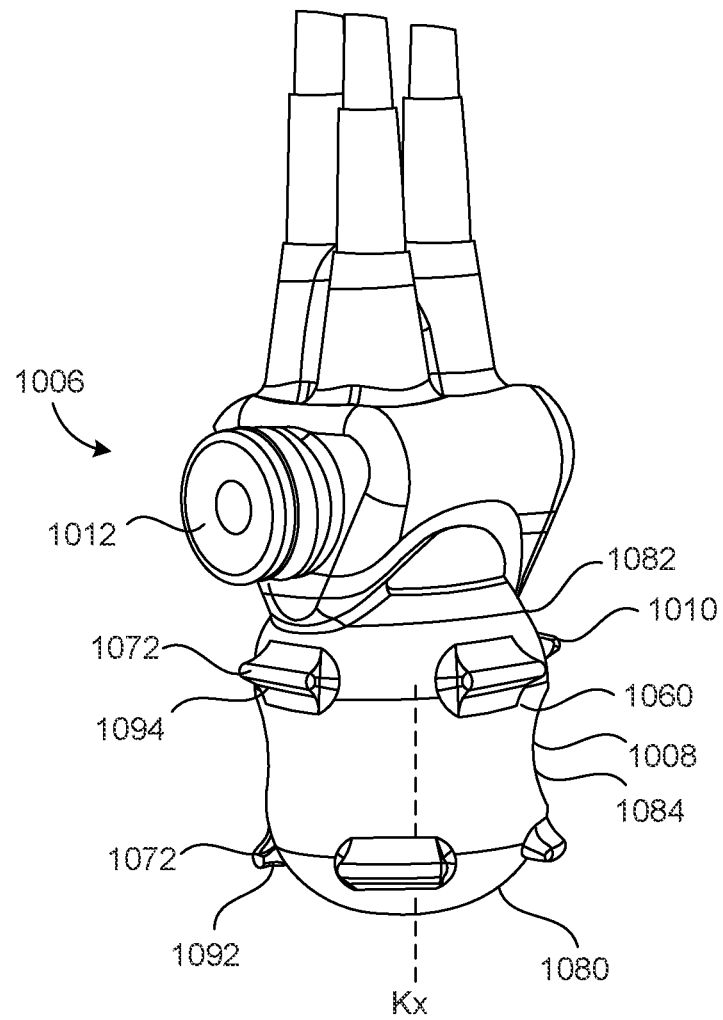

FIG. 12 illustrates a pump assembly 1006 of a penile implant according to an embodiment. In the illustrated embodiment, the pump bulb 1008 includes an outer surface 1060. The pump bulb 1008 also includes an inner surface. The inner surface is disposed opposite the outer surface 1060. The inner surface defines the cavity that is configured to house or receive the fluid as it is passed through the penile implant.

The pump assembly 1006 includes a control feature or member 1010. In the illustrated embodiment, the pump assembly 1006 includes a plurality of projections that form the control feature or member 1010. The pump assembly 1006 includes a plurality of horizontal projections 1072. The horizontal projections 1072 are coupled to and extend from the outer surface 1060 of the pump bulb 1008. In some embodiments, the horizontal projections 1072 are integrally or unitarily formed with the pump bulb 1008.

In the illustrated embodiment, the projections 1072 each have a height H (the distance that the projections 1072 extend from the outer surface 1060 of the pump bulb 1008), a length L, and a width W. The lengths of the projections 1072 are larger or greater than the widths of the projections 1072. In the illustrated embodiment, the length L of each of the projections defines an axis K of the projections. Specifically, the length L extends along the axis K.

The pump bulb 1008 has a first end portion 1080 and a second end portion 1082 disposed opposite the first end portion 1080. The pump bulb 1008 defines an axis KX that extends from the first end portion 1080 to the second end portion 1082. In the illustrated embodiment, the projections 1072 extend substantially linearly in the length direction (along the length L and in the direction of the axis F). In the illustrated embodiment, the axis K is substantially perpendicular to the axis KX.

In the illustrated embodiment, the pump assembly includes a first series of horizontal projections 1092 and a second series of horizontal projections 1094. Each series of projections extend around a circumference of the pump bulb 1008. In the illustrated embodiment, the first series of projections 1092 are disposed proximate or near the first end portion 1080 of the pump bulb 1008. The second series of projections 1092 are disposed proximate or near the second end portion 1082 of the pump bulb 1008. The projections of the first series of projections 1092 are offset (or not horizontally aligned with) from the projections of the second series of projections 1094.

In some embodiments, the pump assembly includes a different number of series of horizontal projections (such as more than two or less than two).

In the illustrated embodiment, different locations of the pump bulb 1008 have different sizes. For example, the diameter of the pump bulb 1008 varies at different locations along the pump bulb 1008. In the illustrated embodiment, the pump bulb 1008 has a first size at the first end portion 1080, a second size at the second end portion 1082, and a third size at a location 1084 that is between the first end portion 1080 and the second end portion 1082. The first size is larger than the third size. The second size is larger than the third size. In some embodiments, the first size and the second size are the same. In other embodiments, the first size is different than the second size.

In the illustrated embodiment, the projections 1072 and/or the sizing of the pump bulb 1008 may help prevent the pump bulb 1008 from slipping during actuation of the pump bulb 1008 by the user. The projections and/or the sizing of the pump bulb may also help prevent the pump bulb 1008 from rotating during the pumping or actuation by the user. In some embodiments, the projections 1072 help or facilitate the locating of the deflation mode actuator 1012.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. An inflatable implant, comprising:
a fluid reservoir;
an inflatable member; and
a pump assembly including a pump bulb, the pump bulb having an outer surface, the pump bulb having a horizontal projection disposed on the outer surface and a vertical projection disposed on the outer surface, the horizontal projection having an end, the vertical projection having a first end and a second end opposite the first end, the vertical projection extending linearly from the first end of the vertical projection to the second end of the vertical projection, the end of the horizontal projection being spaced from the first end of the vertical projection and being spaced from the second end of the vertical projection.

2. The inflatable implant of claim 1, wherein the pump bulb includes a plurality of horizontal projections disposed on the outer surface.

3. The inflatable implant of claim 1, wherein the pump bulb includes at least 4 horizontal projections disposed on the outer surface.

4. The inflatable implant of claim 1, wherein the pump bulb includes at least 6 horizontal projections disposed on the outer surface.

5. The inflatable implant of claim 1, wherein the pump bulb includes a plurality of vertical projections disposed on the outer surface.

6. The inflatable implant of claim 1, wherein the pump bulb includes at least 4 vertical projections disposed on the outer surface.

7. The inflatable implant of claim 1, wherein the pump bulb includes at least 6 vertical projections disposed on the outer surface.

8. The inflatable implant of claim 1, wherein
the horizontal projection has a height, a width, and a length, the length of the horizontal projection being greater than the width of the horizontal projection, the length of the horizontal projection defining an axis,
the vertical projection has a height, a width, and a length, the length of the vertical projection being greater than the width of the vertical projection, the length of the vertical projection defining an axis,
the axis of the horizontal projection being perpendicular to the axis of the vertical projection.

9. The inflatable implant of claim 1, wherein the horizontal projection includes a curved portion.

10. The inflatable implant of claim 1, wherein the pump bulb has a first end portion, a second end portion, and a middle portion disposed between the first end portion and the second end portion, the first end portion has a first size, the middle portion has a second size, the first size being greater than the second size.

11. The inflatable implant of claim 1, wherein the pump bulb has a first end portion, a second end portion, and a middle portion disposed between the first end portion and the second end portion, the first end portion has a first size, the middle portion has a second size, the second end portion has a third size, the first size being greater than the second size, the third size being greater than the second size.

12. The inflatable implant of claim 1, wherein the pump bulb has a first end and a second end opposite the first end, a conduit connector extends from the first end of the pump assembly and is configured to fluidically couple the pump assembly to the inflatable member, the pump bulb being disposed at the second end of the pump assembly.

13. An inflatable implant, comprising:
a fluid reservoir;
an inflatable member; and
a pump assembly including a pump bulb, the pump bulb having an outer surface, the pump bulb having a horizontal projection disposed on the outer surface, a vertical projection disposed on the outer surface, the vertical projection having a first end and a second end spaced from the first end, the vertical projection extending linearly from the first end of the vertical projection to the second end of the vertical projection, the horizontal projection being spaced from the vertical projection, the horizontal projection includes a length and a width, the length of the horizontal projection being larger than the width of the horizontal projection, the horizontal projection having a first end and a second end spaced from the first end, the horizontal projection being curved along the length of the horizontal projection between the first end of the horizontal projection and the second end of the horizontal projection.

14. The inflatable implant of claim 12, wherein the horizontal projection is a first horizontal projection, the pump bulb having a second horizontal projection disposed on the outer surface, the first horizontal projection is offset horizontally and vertically from the second horizontal projection.

15. The inflatable implant of claim 13, wherein the pump bulb has a middle portion disposed between a first end portion and a second end portion, the first end portion has a first size, the middle portion has a second size, the first size being greater than the second size.

16. The inflatable implant of claim 13, wherein the pump bulb has a middle portion disposed between a first end portion and a second end portion, the first end portion has a first size, the middle portion has a second size, the second end portion has a third size, the first size being greater than the second size, the third size being greater than the second size.

17. The inflatable implant of claim 13, wherein the pump bulb is configured to be disposed within a scrotum of a patient.

18. The inflatable implant of claim 13, wherein the horizontal projection is a first horizontal projection, the pump bulb having a second horizontal projection disposed on the outer surface, the pump bulb has a first end portion and a second end portion opposite the first end portion, the first horizontal projection being disposed proximal the first end portion, the second horizontal projection being disposed proximal the second end portion.

19. The inflatable implant of claim 13, wherein the pump bulb has a first end and a second end opposite the first end, a conduit connector extends from the first end of the pump assembly and is configured to fluidically couple the pump assembly to the inflatable member, the pump bulb being disposed at the second end of the pump assembly.

20. An inflatable implant, comprising:
a fluid reservoir;
an inflatable member; and
a pump assembly including a pump bulb, the pump bulb having an outer surface, the pump bulb having a first horizontal projection disposed on the outer surface, a second horizontal projection disposed on the outer surface, a vertical projection disposed on the outer surface, the vertical projection having a first end portion and second end portion, the vertical projection extending linearly from the first end portion of the vertical projection to the second end portion of the vertical projection, the first horizontal projection being spaced from the vertical projection, the first horizontal projection includes a length and a width, the length of the first horizontal projection being larger than the width of the first horizontal projection, the first horizontal projection having a first end and a second end spaced from the first end, the first horizontal projection being curved along the length of the first horizontal projection between the first end of the first horizontal projection and the second end of the first horizontal projection, the first horizontal projection being offset vertically from the second horizontal projection.

\* \* \* \* \*